United States Patent
Smith

(10) Patent No.: US 11,969,389 B2
(45) Date of Patent: Apr. 30, 2024

(54) INTEGRATED LOWER BACK TREATMENT SYSTEMS

(71) Applicant: David Andrew Smith, Toronto (CA)

(72) Inventor: David Andrew Smith, Toronto (CA)

(*) Notice: Subject to any disclaimer, the term of this patent is extended or adjusted under 35 U.S.C. 154(b) by 399 days.

(21) Appl. No.: 17/180,796

(22) Filed: Feb. 21, 2021

(65) Prior Publication Data

US 2021/0169732 A1 Jun. 10, 2021

Related U.S. Application Data

(60) Provisional application No. 63/073,996, filed on Sep. 3, 2020.

(51) Int. Cl.
*A61H 23/00* (2006.01)

(52) U.S. Cl.
CPC ...... *A61H 23/00* (2013.01); *A61H 2201/0119* (2013.01); *A61H 2201/1626* (2013.01); *A61H 2201/165* (2013.01); *A61H 2201/1654* (2013.01)

(58) Field of Classification Search
CPC .... A61H 23/00; A61H 15/00; A61H 15/0092; A61H 2201/0119; A61H 2201/1626; A61H 2201/1654; A61H 2201/0107; A61H 2201/0134; A61H 2201/0157; A61H 2201/1623; A61H 2005/081; A61F 5/028
See application file for complete search history.

(56) References Cited

U.S. PATENT DOCUMENTS

| | | |
|---|---|---|
| 4,552,135 A | 11/1985 | Racz |
| 4,627,109 A | 12/1986 | Carabelli |
| 5,039,158 A | 3/1991 | Maier |
| 5,577,995 A * | 11/1996 | Walker ............... A61H 15/0092 601/118 |
| 6,398,694 B1 * | 6/2002 | Bountourakis .. A63B 21/00069 601/134 |
| 7,001,350 B2 | 2/2006 | Grosso |

(Continued)

FOREIGN PATENT DOCUMENTS

| | | |
|---|---|---|
| GB | 2437053 | 10/2007 |
| JP | 2000185063 | 7/2000 |

(Continued)

OTHER PUBLICATIONS https://www.amazon.com/Back-Support-Pillow-RS5-Accessories/dp/B07NCBX8GG/ref=sr_1_2?dchild=1&keywords=rs5+lumbar&qid=1613517415&sr=8-2.

*Primary Examiner* — Michael R Reid
*Assistant Examiner* — Nathan M Le

(57) ABSTRACT

An integrated lower back treatment system is provided. The system includes a central core. The system also includes attachment devices positionable on longitudinal ends of the core. The system further includes a strap, wherein an end of the strap connects with a longitudinal end of the core with the attachment device and an opposite end of the strap connects to an opposite longitudinal end of the core with another attachment device. Additionally, the system includes padding, wherein the padding assembly includes padding arranged to allow the padding to connect and form a shape over the core and wherein the padding has differing firmness characteristics such that when the padding is rotated about a longitudinal axis of the core, a user of the integrated lower back treatment system will experience different firmness values dependent upon a position of the rotated padding on a lower back of the user.

13 Claims, 9 Drawing Sheets

(56) References Cited

U.S. PATENT DOCUMENTS

| | | | |
|---|---|---|---|
| 7,291,101 B2* | 11/2007 | Deal | A63B 21/0004 |
| | | | 482/121 |
| D822,772 S * | 7/2018 | Jorgenson | D24/211 |
| 10,285,899 B2* | 5/2019 | Jones | A63B 23/0216 |
| 2011/0313333 A1* | 12/2011 | Nicholson | A61H 15/0092 |
| | | | 601/120 |
| 2013/0085426 A1* | 4/2013 | Brodsky | A61N 5/0619 |
| | | | 601/128 |
| 2013/0178768 A1* | 7/2013 | Dalebout | A61H 15/0092 |
| | | | 601/118 |
| 2014/0128786 A1* | 5/2014 | Ross | A61H 15/0092 |
| | | | 601/118 |
| 2016/0074273 A1* | 3/2016 | Mallory | A61H 15/00 |
| | | | 601/118 |
| 2016/0310352 A1* | 10/2016 | Chen | A61H 15/0092 |
| 2019/0125623 A1* | 5/2019 | Spratt | A61H 15/0092 |

FOREIGN PATENT DOCUMENTS

| | | |
|---|---|---|
| JP | 5626657 | 11/2014 |
| JP | 3223462 U | 10/2019 |

\* cited by examiner

INTEGRATED LOWER BACK TREATMENT SYSTEMS

RELATED APPLICATIONS

This application claims priority to U.S. Provisional Application No. 63/073,996 filed Sep. 3, 2020. The entire contents of the above application are hereby incorporated by reference as though fully set forth herein.

FIELD OF THE INVENTION

The present invention relates generally to back treatment systems, and more particularly, to integrated lower back treatment systems which augment a person's ability to alleviate lower back pain in response to natural and environmental conditions and to provide effective pain prevention mechanisms.

BACKGROUND OF THE INVENTION

Many treatments, methods and systems have been used in unsuccessful attempts to alleviate lower back pain created by natural, manmade, and other environmental conditions. These treatments, systems and methods have not been reliable or effective. Many of the unsuccessful treatments are cumbersome, costly and fail to address the variability of the human body in various seated settings.

As the world's commercial landscape evolves, so has the working environment of today's labor force. More and more workers force find themselves carrying out functions while seated. The percentage of time spent executing tasks while seated has been steadily increasing. As such, the prevalence of medical problems related to individuals sitting for longer periods has risen. Many of these medical problems are lower back related.

Throughout the world, the problem of providing adequate remedies to address back pain has been a longstanding issue. Quite often remedies are provided, however they are not fully effective. Many devices and systems failed to provide adequate relief because sometimes lumbar solutions are often made of single density padding and therefore are not simultaneously variable in their applied diameter and firmness. Other solutions have unsuccessfully attempted to solve lower back pain solely through the use of some type of inflatable bladder employing various versions of air or fluid filled sacs. These solutions are similarly unable to provide proper relief because they are cumbersome, complex, and involve employing some combination of air, gaseous fluid, liquid and some manual or automated pumping action for a desired effect. Still other solutions seek to make a lumbar support adjustable by allowing removable pads. These solutions also failed to provide adequate relief because they require the user to reconfigure the device and lack a wide range of diameter variation.

Many of the unsuccessful devices and systems included extra costs associated with purchasing and transporting multiple items to satisfy a single need. Additionally, these unsuccessful attempts of providing adequate lower back pain relief mechanisms quite often involve excessive manufacturing costs associated with complex apparatus.

Further, previous unsuccessful attempts included removable pads. These solutions also fail to provide efficient and effective pain prevention mechanisms and pain alleviation remedies because they require the user to continuously manually reconfigure the device and many of these ineffective systems lack a wide range of diameter variations.

Lower back pain sufferers have the additional consequence of the negative impacts to productivity due discomfort. Individuals, whether active in the workforce or not, who are experiencing lower back pain, often seek remedies through medical means including clinic/hospital visits as well as over-the-counter and prescribed medicine. These conditions affect all members of society because the cost of these remedies has a downstream effect of being borne by taxpayers which reduces overall productivity.

It is estimated that about 80% of adults will experience Lower Back Pain (LBP) during their lifetime. Additionally, LBP accounts for about 3.3 million emergency room visits annually in the United States. The World Health Organization anticipates the rate of LBP will increase over the next 20 years as our aging population age places increased burden on health care systems and accompanying losses to productivity.

Additionally, past attempts have failed to provide a singular device for the alleviation of back pain for a wide variety of body types and seating environments.

Accordingly, there is an established need for a lower back treatment system which solves at least one of the aforementioned problems. Further, there is an established need for integrated lower back treatment systems which can address providing individualized lower back pain prevention mechanisms and remedies to alleviate pain.

SUMMARY OF THE INVENTION

According to an aspect of the present invention, integrated lower back treatment systems are provided. These innovations include new, useful, and non-obvious treatment systems which provide back pain prevention mechanisms and back pain remedies.

An integrated lower back treatment system is provided. The system includes a central core. The system also includes attachment devices positionable on longitudinal ends of the central core. The system further includes a strap, wherein an end of the strap connects with a longitudinal end of the central core with the attachment device and an opposite end of the strap connects to an opposite longitudinal end of the central core with another attachment device. Additionally the system includes a padding assembly, wherein the padding assembly includes a plurality of padding segments arranged to allow the plurality of padding segments to mate with each other forming a shape over the central core and wherein the padding segments are structured with differing firmness characteristics such that when the plurality of padding segments are rotated about a longitudinal axis of the central core, a user of the integrated lower back treatment system will experience different firmness values dependent upon a position of the rotated padding segments on a lower back of the user.

According to another aspect of the present invention, the system can include a portable modular padded belt for providing support to the lower spine and surrounding paralumbar musculature of the wearer while seated. The system can also include a strap assembly and a plurality of padding layers of solid dispersed media. The padding can be configured by the user to provide an individualized customized support to the lower back to effect pain relief.

In yet another aspect, the system can include a singular device for the alleviation of back pain for a wide variety of body types and seating environments. The system can also include a lumbar support that provides padding firmness variability. Further, the system can include a device with an adjustable diameter. The system can also be designed to be lightweight for easy portability. Additionally, the system can include a Modular padded Lumbar Support, which can be made up of a strap assembly and padding.

In an embodiment, the system can be configured to avoid the hassles and extra costs associated with purchasing and transporting multiple items to satisfy a single need. The system can also include a device that eliminates the manufacturing costs associated with complex apparatus. Further, the system can be configured to address aforementioned deficiencies by providing a singular device that features padding firmness adjustability, diameter variability, is lightweight, and economical to manufacture.

In another embodiment, the system can also include devices arranged for changeable variables that may satisfy users who were often frustrated by having to buy/try several lumbar support components to alleviate back pain. The system can include features which reduces the commercial risks of a purchase of a lumbar support by allowing for a plurality of firmness preferences, which vary from user to user. The system can include capabilities to allow for a variety of diameter size demands, which are unique to each individual and seated environment whether at work or otherwise.

In yet another embodiment, the system can include components which reduce the need for higher complexity and added weight resulting from inflatable solution components, which discourage easy portability.

In an aspect, the system can include integrated components which simultaneously provide for padding density variability, a changeable diameter, in total has a relatively low weight, and has lower manufacturing costs due to elimination of inflation apparatus in a single lumbar device.

In another aspect, the system can also include devices with components configured with free-form solid dispersed media and panelized with semi-annular, elliptical, or less than circular, 3-dimensional bodies made from developable strips.

In yet another aspect, the system can include a strap assembly. The strap assembly can be configured to provide to the wearer the ability to firmly position the lumbar support against the small of their back using either an appropriate back rest or their body.

In embodiments, the system can include a strap assembly arranged to accommodate the core which is centrally located and affixed between 2 straps. The core can be structured to provide resisting tension forces when the user is securing the device to any body and to delimit the firmness settings of the Modular padding Strips as described hereinafter.

In embodiments, the system can include a core with a plurality of shapes. The core can be any 3-dimensional oblong shape such as, but not limited to, an ovoid, triangular prism, 3 dimensional cylinder, braided cord or the like where the shape may be longer than it is wide and sufficiently long enough to traverse the length of the assembled device. The core can be resistant to compression across the cross-section.

In embodiments, the system can include a strap which can be made of any flexible material with a means to secure or fasten to the wearer, a seat or other suitable seating device.

In embodiments, the system can include modular padding strips. The modular padding strips can include padding. The padding can be made of solid dispersed media In embodiments, the padding can be a configurable medium for delivering comfort to the user's back. The padding can be connected to the belt in a manner that allows the user to position the padding in a desired position. The dimensions of the padding can be sufficient to permit relief to users suffering from lower back pain. The padding can be shaped to allow the diameter to increase or decrease as per the user's wishes through layering (paneling). The layering can be achieved using any means that permit panels to be held adjacent adjoining one to another during configuration working outwards from the center of the device. Fastening may utilize mechanisms such as, but not limited to hook and loop, or interlocking shapes of the padding In embodiments, the padding can be a plurality of solid dispersed media layers. The media can include various densities and may be arranged by the user to effect differing firmness depending on how the padding is arranged in series.

In embodiments, the system can include padding designated as 'firm' and can be arranged in series with a padding designated as 'soft' to facilitate user preferences.

In embodiments, the system can include a strap assembly which includes a core. The core can be any 3-dimensional oblong shape such as, but not limited to an ovoid, triangular prism, 3-D semi-circle, cylinder or any of a plurality of shapes wherein the shape can be longer than it is wide and sufficiently long enough to traverse the length of the assembled device. In embodiments, the strap can be configured to attach the system to a chair or to a user's torso.

In embodiments, the system can include a core which can be made of a rigid/semi-rigid material. The core may be solid or hollow permitting enhancements to further augment the invention such as an introduction of heat retention/generation devices, cooling, vibration devices, transducers or any other device that may improve user enjoyment. The core may also be used to augment the structural strength of the device.

In embodiments, the core may be constructed of any material that meets an application's demands such as a type of plastic, metal, synthetic cord or other solid material which provides structural support. Ends of the core can employ a plurality of means of attaching a strap, belt or other attachment mechanism. The mechanism attaching the core to the strap may be detachable. The strap may be any type of belt or strap which can be lengthened or shortened to suit the user's needs. The padding may be shaped in any way that allows flexibility for padding firmness and diameter flexibility. The innermost padding may be a semi-annular tube design around the core. A subsequent padding layer may surround the innermost padding as a layer of padding rolled by the user to change firmness and diameter parameters.

In embodiments, the system can include a plurality of individual padding layers, padding shapes, and/or padding densities.

In embodiments, the padding layers can have a means of retaining cohesion during assembly. The padding layers can be affixed to each other by means of various fastening methods such as, but not limited, to hook and loop.

In embodiments, cohesion of the padding layers may be accomplished by the shape of the padding layers, strips, or similar building parts to be assembled without the use of additional elements provided with holes, grooves, or protuberances which can dovetail with primary projections fitting by friction in complementary spaces between secondary projections, for example using connecting mechanisms such as sidewalls (LEGO®).

In embodiments, structural cohesion may also be accomplished through external means such as a container or a sleeve. The container or sleeve can be made up of a flexible material permitting the accommodation of the core and padding. The container may have a means of tightening the fit around the padding such as a drawstring on either or both ends, a zipper for permitting expansion or other devices that allow increase or decrease in volumetric space.

In embodiments, the space between the exterior facing surface and the interior facing surface may be occupied with one or more plies of material and/or one or more subcompartments or pockets for storing items. The device can be made up of a strap assembly made of a core and a strap, a first padding portion, a second padding portion, a third padding portion, a fourth padding portion, and an inner container and an outer container. These components can include the core and can be the innermost portion of the lumbar device. The core can serve the purpose of resisting tension forces when the user is securing the device to an external seat or a human body. The core can be a synthetic braided cord where the shape can be longer than it is wide and sufficiently long enough to traverse the length of the assembled device.

In embodiments, both ends of the cord can employ a 'D' ring or carabiner to be coupled with a strap. The cord can be centrally attached between at least 2 straps. The strap can be made up of cotton/polyester fabric. The strap can include two independent pieces. One end of each strap can have a 'D' ring for coupling with the 'D' ring carabiner on one end of the core. One strap can be attached to the core using said 'D' ring coupling. A second strap can similarly be attached using a 'D' ring coupling to the 'D' ring carabiner on the opposite end of the core. The free end of each strap, not coupled to the core, can have a snap hook buckle used to fasten to each other. The strap can have a length suitable enough to wrap around a human body and be secured using said snap hook buckle. Further, the strap can have a length sufficient to wrap around a seat and be secured using said snap hook buckle.

In embodiments, the core together with the attached 2 straps can constitute the strap assembly. The padding can have the purpose of providing comfort to the user. Further, the padding can be configured to provide specific firmness and/or hardness areas spatially oriented to provide preventive measures for potential future back pain. The padding can include a plurality of layers. The layers can include media material such as but not limited to memory foam, polyurethane foam, foam padding, pocket springs, latex, organic and/or synthetic fibers.

In embodiments, the innermost padding layer can be comprised of the core surrounded by the first padding portion and the second padding portion.

In embodiments, the innermost padding layer can be configured to allow the core to fit snugly inside diameter of a void defined by the fitting of two opposing channels.

In embodiments, the first padding portion and the second padding portion can be complimentary to each other. The first padding portion and the second padding portion can be identically shaped. The first padding portion and the second padding portion can be identically sized. The first padding portion length and the second padding portion length can be shorter than the core with a distance sufficient to allow user access to the fastening mechanisms that couple the strap to the core simultaneously on opposing ends. The first padding portion and the second padding portion can each be a semi-annular 3-dimensional shape similar to a 3-dimensional half shaped circle body.

In embodiments, the first padding portion and the second padding portion can each have differing firmness characteristics. The first padding portion can have a foam density of very firm hardness. The second padding portion can have a foam density of a firm hardness.

In embodiments, the first padding portion can have a central channel that traverses the entire length of the pad. The first padding portion channel can be shaped as a half cylinder with a radius equal to the outer radius of the core. As hereinabove noted, the core fits snugly inside the diameter of the first padding channel or fits snugly inside the diameter of the second padding channel.

In an aspect, the system can include a second padding portion which can have a central channel that traverses the entire pad in size and shape and can be identical to the channel on the first padding portion.

In an aspect, the system can include complimentary opposing hook and loop fasteners which can be attached to the non-curved faces of the first padding portion and the second padding portion so that they are an equal distance from the edges of each respective padding.

In an aspect, the system can include hook and complimentary loop fasteners which can be identical in dimensions. The hook and loop can be sized to permit the first padding portion to be secured to the second padding portion with the core in place so that the core cannot slide freely from the said void as formed by the channel of the first padding portion and the second padding portion. The void formed from the first padding portion being secured against the second padding portion are hereinafter be referred to as inner hollow. Further, said hook and loop fasteners can be sized to permit the average adult human to separate the first padding portion from the second padding portion without undue difficulty.

In an aspect, the system can include a first padding portion which can have 2 hook fasteners affixed transversely on the flat face and 2 loop fasteners affixed on the opposite face transversely. The complimentary second padding portion can have 2 hook fasteners affixed transversely on the flat face and 2 loop fasteners affixed on the opposite face transversely. The hook and loop fasteners can be positioned in a manner that allows the hook of the first padding portion to fasten to the opposing loop on the second padding portion.

In an aspect, the system can include a method wherein during assembly, either the first padding portion or the second padding portion can be selected. The core can be laid inside the channel of the selected padding portion. The complimentary padding portion can be attached via hook and loop to form a complete padded layer. It is not a requirement the strap be affixed during the assembly of the core and innermost padding layer.

In an aspect, the system can include materials which provide a pliant nature to the padding and the core materials, and there can be some minor flexibility in absolute dimensions so long as these differences do not result in a loose fit wherein the core can slide freely through the inner hollow. Further, deviation in the dimensions of the core and the first padding portion and the second padding portion and respective channels can and should preferentially allow the first padding and second padding to be securely attached by hook and loop when the core has been placed centrally within the inner Hollow.

In an aspect, the system can include an assembled core and inner padding layers and can be referred to as the inner padding assembly.

In an aspect, the inner container can be a flexible membrane structure which can have the purpose of maintaining the configuration of the inner padding assembly. The inner container can be made of a synthetic polyester/spandex blend in a ventilated mesh configuration. When not in use, the inner container can have an amorphous shape.

In an aspect, the system can include an inner container which can have a cylindrical shape, when not in use. The length of the container can be long enough to permit encapsulation of the inner padding assembly when in a slightly stretched (stressed) state. The inner container diameter can be similar to the outer diameter of the inner padding assembly with enough diameter to permit encapsulation of the inner padding assembly when in a slightly stretched (stressed) state.

In an aspect, the system can include a top and a bottom (base) of the inner container which can be circular. The top and said base can each have identical diameter holes that are smaller than the total diameter of the cylinder and large enough to permit the passage of the inner padding assembly when stretched. Each open-ended hole can have an elastic woven into the outer edge of the hole to partially close access to the inner padding assembly.

In an aspect, each elasticized hole closure must not frustrate the accessibility of either or both of the 'D' ring carabiners on the core.

In an aspect, the user can have the option to use the inner padding assembly due to diameter considerations for comfort and pain relief. The user can use the device by enclosing said inner padding assembly using the inner container as described hereinbefore and attaching said straps on both ends of said core.

In an aspect, the outer padding layer can be comprised of the inner padding assembly surrounded by the third padding portion and the fourth padding portion.

In an aspect, the outermost padding layer can be configured to allow the inner padding assembly to fit snugly inside diameter of a void defined by the fitting of two opposing channels.

In an aspect, the system can include a third padding portion and a fourth padding portion which can be complimentary to each other. The third padding portion and the fourth padding portion can be identically shaped. The third padding portion and the fourth padding portion can be identically sized. The third padding portion length and the fourth padding portion length can be equal to the length of the first padding portion. The third padding portion and the fourth padding portion can each be a semi-annular 3-dimensional shape similar to a 3-dimensional half shaped circle body. The third padding portion and the fourth padding portion can each have differing firmness characteristics. The third padding portion can have a foam density of medium. The fourth padding portion can have a foam density of soft.

In an embodiment, the third padding portion can have a central channel that traverses the entire length of the pad. The third padding portion channel can be shaped as a half cylinder with a radius equal to the outer radius of the innermost padding layer. As hereinabove noted, the innermost padding layer can fit snugly inside the diameter of the third padding channel or fit snugly inside the diameter of the fourth padding channel.

In an aspect, the fourth padding portion can have a central channel that traverses the entire pad in size and shape identical to the channel on the third padding portion.

In an aspect, the system can include complimentary opposing hook and loop fasteners which can be attached to the non-curved faces of the third padding portion and the fourth padding portions so that they are an equal distance from the edges of each respective padding.

In an aspect, the hook and complimentary loop fasteners can be identical in dimensions. The hook and loop can be sized to permit the third padding portion to be secured to the fourth padding portion with the inner padding assembly in place so that the inner padding assembly cannot slide freely from the said void as formed by the channel of the first padding portion and the second padding portion. The void formed from the third padding portion being secured against the second padding portion is hereinafter be referred to as outer hollow.

In an embodiment, the hook and loop fasteners can be sized to permit the average adult human to separate the third padding portion from the fourth padding portion without undue difficulty.

In an embodiment, the third padding portion can have 2 hook fasteners affixed transversely on the flat face and 2 loop fasteners affixed on the opposite face transversely. The complimentary fourth padding portion can have 2 hook fasteners affixed transversely on the flat face and 2 loop fasteners affixed on the opposite face transversely. The hook and loop fasteners can be positioned in a manner that allows the hook of the third padding portion to fasten to the opposing loop on the fourth padding portion. The hook and loop fasteners can be positioned in a manner that allows the hook of the third padding portion to fasten to the opposing loop on the fourth padding portion. During assembly, either the third or fourth padding portion are selected. The innermost padding layer can be laid inside the channel of selected padding portion. The complimentary padding portion can be attached via hook and loop to form a complete the outer padded layer. It is not a requirement the strap be affixed during the assembly of the innermost padding layer and outermost padding layer.

In an embodiment, the system can include materials with a pliant nature of the outermost padding and the innermost padding layer materials, where there can be some minor flexibility in absolute dimensions so long as these differences do not result in a loose fit, wherein the innermost padding layer can slide freely through the channel. Further, deviation in the dimensions of the innermost padding layer and the third padding portion and the fourth padding portion and respective channels can allow the third padding and fourth padding to be securely attached by hook and loop when the innermost padding layer has been placed centrally within the channel.

In embodiments, the assembled inner padding assembly and outer padding layer can be referred to as a padding assembly. The outer container can be a flexible membrane structure which has the purpose of maintaining the configuration of the padding assembly. The outer container can be made of a synthetic polyester/spandex blend in a ventilated mesh configuration. When not in use, the outer container can have an amorphous shape.

In embodiments, the outer container can have a cylindrical shape, when not in use. The length of the outer container can be long enough to permit encapsulation of the padding assembly when in a slightly stretched (stressed) state. The outer container diameter can be similar to the outer diameter of the padding assembly with enough to permit encapsulation of the inner padding assembly when in a slightly stretched (stressed) state.

In embodiments, the top and the bottom (base) of the outer container can be circular. The top and said base each can have identically diameter holes that are smaller than the total diameter of the cylinder and large enough to permit the passage of the padding assembly when stretched. Each open-ended hole can have a drawstring woven into the outer edge of the hole for drawing in the top or the base of the package to selectively close access. It is noted that the drawstring closure preferably must not frustrate the accessibility of either or both of the 'D' ring carabiners on the core.

In embodiments, the inner container and the outer container can be used to maintain the user defined configuration as described in a plurality of embodiments. It is further noted that a user may elect to use inner padding assembly only with the inner container as described hereinafter. It is still further noted that inner container and the outer container can be similar in construction and appearance with the main difference being dimensions. It is still further noted that the inner container need not be assembled (used) when the padding assembly is built.

In embodiments, the straps can be coupled to the padding assembly using said 'D' rings and 'D' ring carabiners. The straps can be configured to secure the padding assembly to the user's back such that the outer padding layer is disposed adjacent the back of the user's neck and transverses the lumbar spine region such that the first direction of expansion is toward and substantially normal to the spine effecting relief.

In embodiments, the system can include devices which can yield at least 8 comfort settings: at least 2 diameter sizes (1 each for inner padding assembly and padded assembly) and at least 6 firmness options (Firm, Very Firm, Firm+Medium, Very Firm+Soft, Very Firm+Medium, Firm+Soft).

In embodiments, the number of firmness and diameter settings can be governed by the sum of padding and Diameter options. The padding can be any shape that makes best use of effecting pain relief by increasing the user selected options. For example, there may be 5 padding layers (2 inner Layers and 3 outer padding Layers) which would increase the padding Firmness options by 2 from aforementioned 6 to 8 for a total of 10 comfort settings. In embodiments, the padding can include material providing cushioning such as but not limited to layered synthetic and/or organic material such as wool and/or cotton. The padding can also include various types of foam, such as memory, closed cell, open cell, gel, latex rubber, lux and other similar materials.

In embodiments, the padding can include bamboo, cotton, polyester, wool or other similar products. Padding may be any combination of a plurality of comfort providing materials.

In embodiments, the padding may also be a gas filled or partially gas filled sac.

In embodiments, the padding may also be in a container housing with flowable loose filled material such as polystyrene foam pieces such as foam peanuts. Further, the padding can be made of regularly/irregularly spaced, protruding gas-filled hemispheres (bubbles).

In embodiments, the padding may be used without any cladding material.

In embodiments, the system can include Foam Specifications and dimensions as referenced herein the accompanying appendices.

In embodiments, the overall shape of the system may be any configuration that supports a human back.

In embodiments, the system can be configured to provide a solution for supporting the lower spinal column at the small of the back by employing a configurable solid dispersed media supported by an inner core.

In embodiments, the system is structured to support the lower spinal column at the small of the back in a variety of firmness configurations wherein lumbar diameter size is configurable. The device can be elegantly constructed which results in lower weight and greater portability. The device can be constructed to provide support for L2 through L5 vertebrae by the application of pressure on the back from variably configurable solid dispersed media which are configurable by the user using various solid dispersed media of differing densities arranged around a supportive inner core.

In embodiments, the system can include varying densities of the solid dispersed media which will permit various firmness and diameter options for the wearer depending on how the user chooses to arrange these densities in series.

In an aspect, the system can be designed to work in conjunction with a belt, strap or other suitable attachment device for securely fixing the invention horizontally across the lumbar region centrally on the users back. Both ends of the device can employ a means for attaching said belt, strap, and other suitable devices.

In an aspect, the system can be designed to be attached to a suitable backrest or optionally wearable for the human body.

In an aspect, the system can be at least bi-directional or multi-directional; the user may wear the device as configured applying comfort using one side and may at any time reverse the device to experience a different firmness setting from the opposite side.

In an aspect, the system can include a portable, removable, adjustable lumbar support device designed to be attached to a suitable backrest or optionally wearable on the human body.

In an aspect, the system can include lumbar support which can be a rigid/semi-rigid inner core surrounded by solid dispersed media of selected densities enclosed within a removable container responsible for ensuring the integrity the invention. The lumbar support can be secured using a belt, strap or other suitable device at the proper level of the lower spine to provide support for the spine in a proper lordosis when the wearer is seated.

In an aspect, the system can include a core which can be a rigid/semi-rigid material. The core may be solid or hollow permitting enhancements to further augment the invention such as: the introduction of heat retention/generation devices, cooling, vibration devices, transducers or any other device that may improve user enjoyment. The core can be any 3-dimensional oblong shape such as: ovoid, triangular prism, 3d semi-circle, cylinder or the like where the shape is longer than it is wide and sufficiently long enough to support a human back. The core may be constructed of any material that meets an application's demands such as a type of plastic, metal or other material choices.

In an aspect, the system can include ends wherein the ends of the core will employ a means of attaching a strap or belt to facilitate the wearer's ability to firmly position the lumbar support against the small of their back using either appropriate back rest or their body.

These and other objects, features, and advantages of the present invention will become more readily apparent from the attached drawings and the detailed description of the preferred embodiments, which follow.

BRIEF DESCRIPTION OF THE DRAWINGS

The features and advantages of the present invention will be better understood when the Detailed Description of the Preferred Embodiments given below is considered in conjunction with the figures provided.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

In an embodiment, the system can include components structured to provide individualized configurable lower back pain relief and lower back pain prevention devices. Examples can be seen in FIGS. 1-9.

Figure 1:
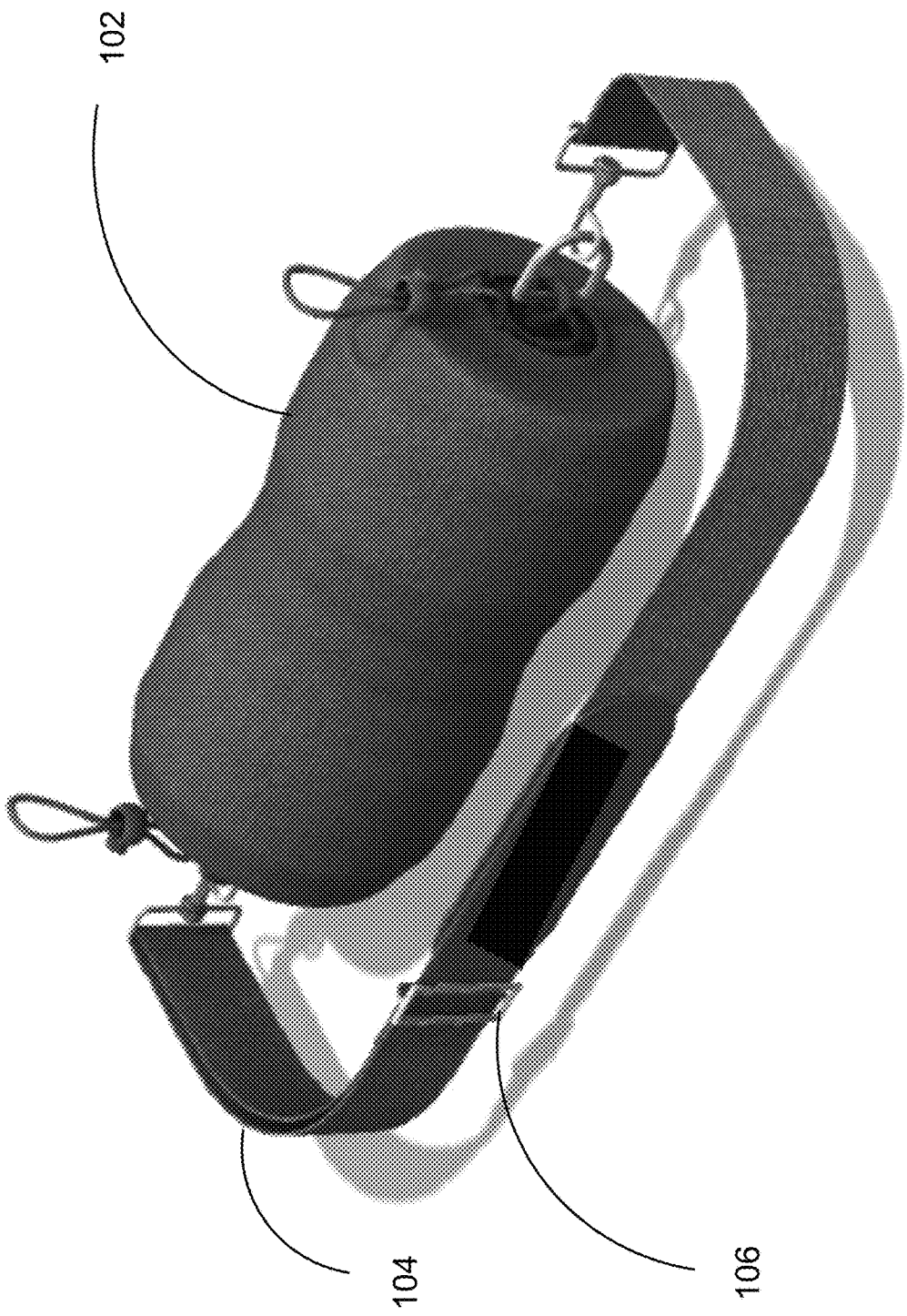
FIG. 1 is a top perspective view of an embodiment of an integrated lower back treatment system.

As seen in FIG. 1, embodiments of the present invention are shown displaying the components assembled and with a strap 104 attached. As displayed, the system 100 can include a contoured assembled padding system with a cover 102. The strap 104 can include a strap adjustment device 106 configured to deploy the system 100 directly on the back of a user or to secure it to another object such as but not limited to car seats, office chairs, walls, and/or working spaces wherein users may allow their backs to place pressure onto the system 100.

Figure 2:
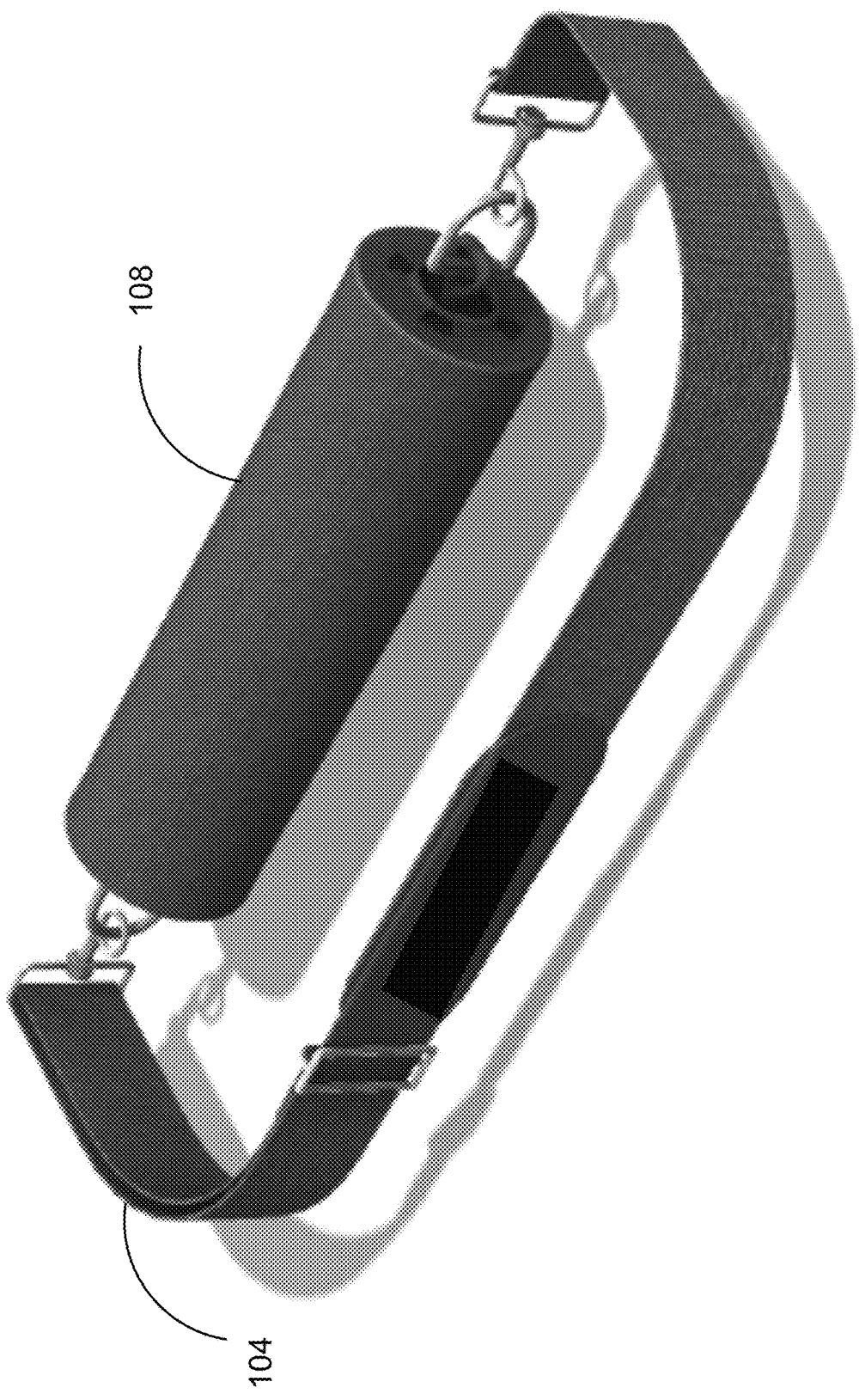
FIG. 2 is a top perspective view showing an inner padding system of an embodiment of the present invention.

As best seen in FIG. 2, the system 100 can function with an assembled inner padding system 108. The assembled inner padding system 108 can connect with the strap 104 in order to deploy the system 100 for use. In embodiments not shown, the inner padding system 108 can consist of a single unitary padding component with homogenous and/or variable density and firmness values throughout the length and radial directions. The system 100 can also include a plurality of inner padding segments each with a discrete and different firmness value.

Figure 3:
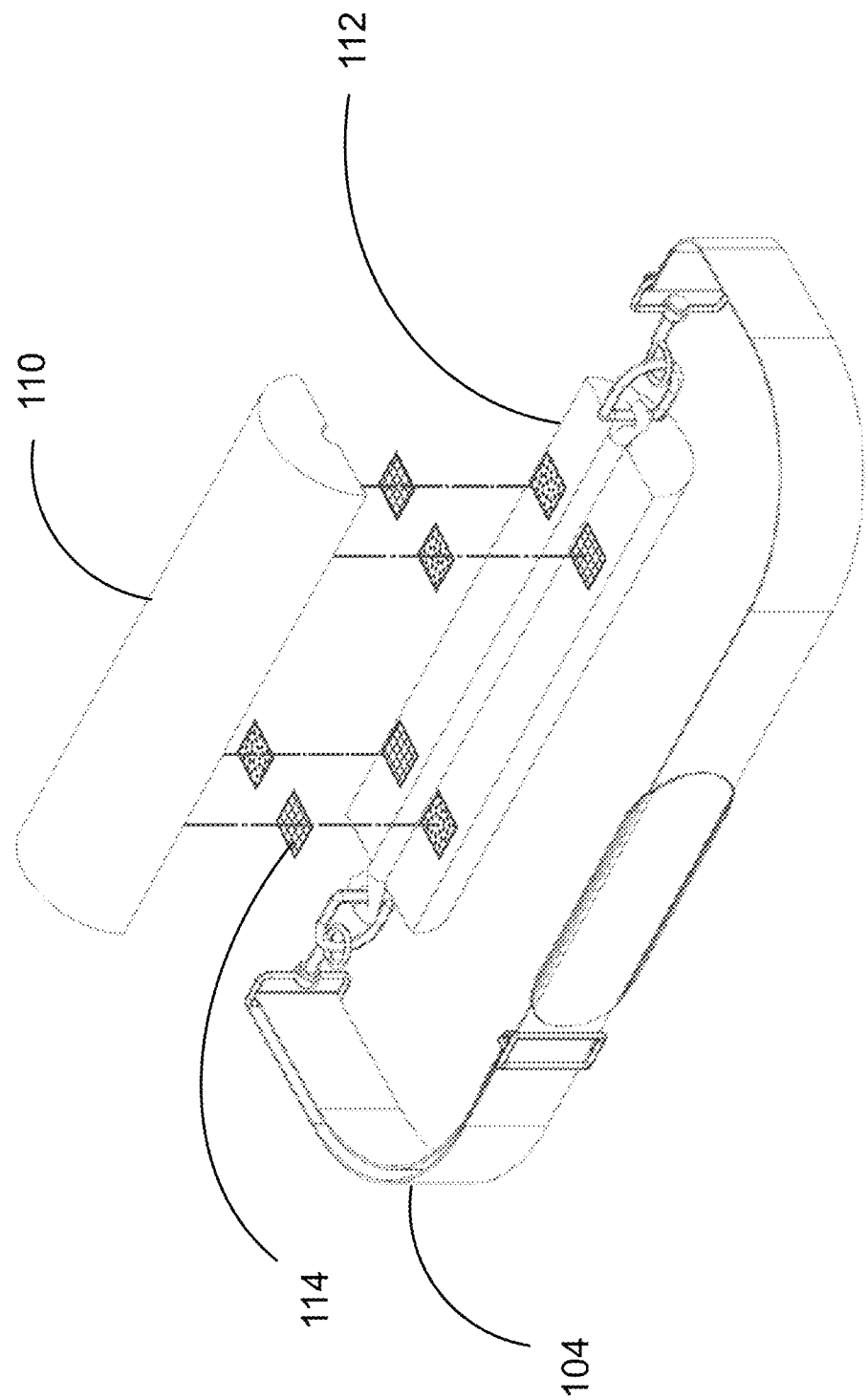
FIG. 3 is a top perspective exploded view showing components of an inner padding system in an embodiment of the present invention.

Turning to FIG. 3 an exploded view of an inner padding system 108 is illustrated. The inner padding system 108 can include two segments, an upper inner padding segment 110 and a lower inner padding segment 112. The lower 110 and upper 112 segments mate with each other to form a longitudinal cylindrical shape with a circular exterior along the axial direction. The upper 110 and lower 112 segments can utilize padding segment attachment devices 114 such as but not limited to hook and loop fasteners, adhesives, and or mechanical fasteners. The inner padding system can include a strap attached to both ends of the inner padding system and designed to be placed directly on a back of a user or on a chair. The inner padding segments can be structured to rotate about its longitudinal axis. The segments can include different firmness values such that a user can rotate the inner segments to obtain different firmness values applied to a user's back.

Figure 4:
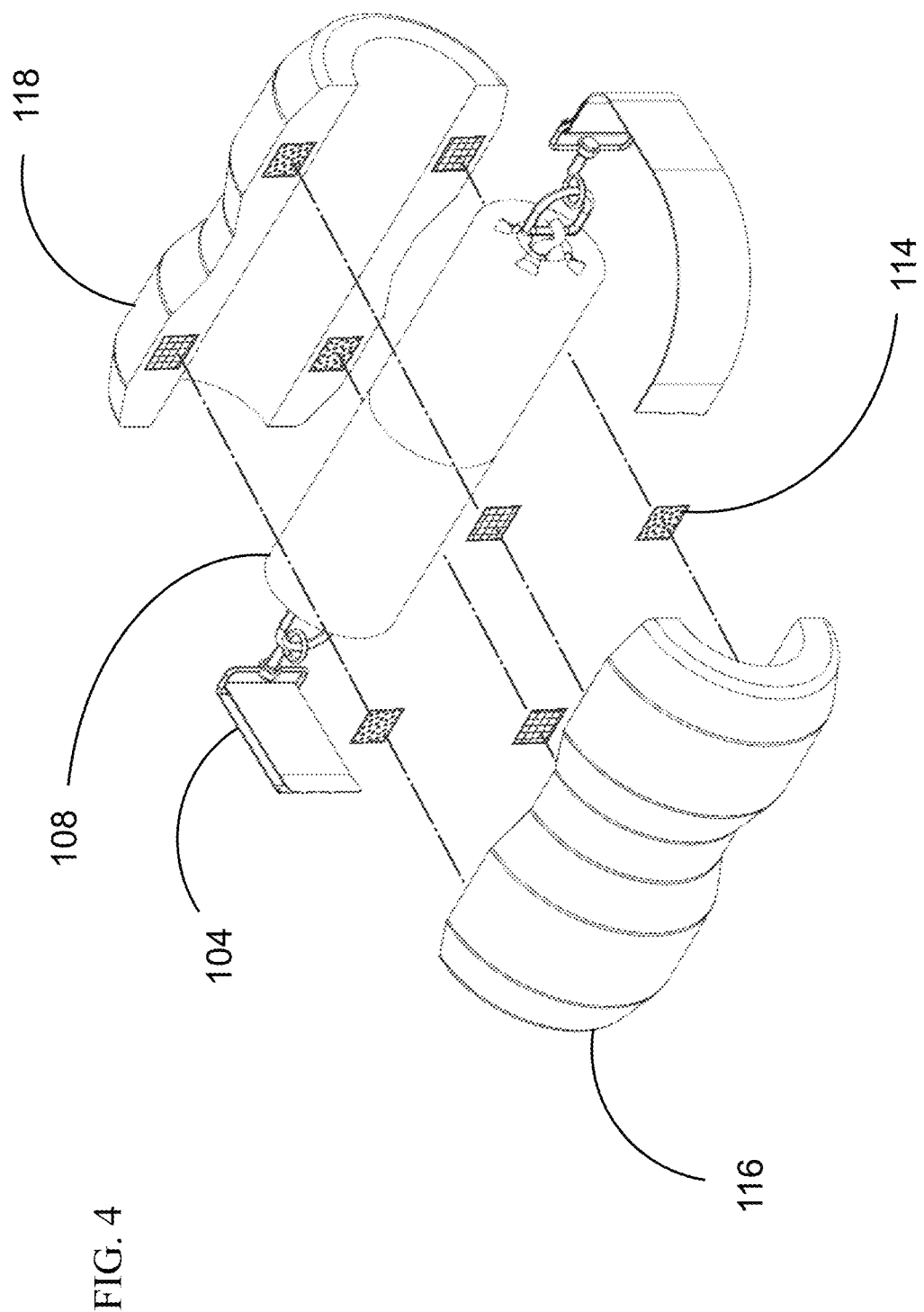
FIG. 4 is a top perspective exploded view showing components of an inner padding system and an outer padding system in an embodiment of the present invention.

FIG. 4 displays an exploded view of outer padding system over an assembled inner padding system 108. The outer padding system can include a left-hand side outer padding segment 116 and a right-hand side outer padding segment 118. In embodiments there can exist a plurality of distinct and discrete outer padding segments each with different firmness values. In embodiments the outer padding segments can rotate about its longitudinal axis. A user can obtain different firmness settings by rotating the outer padding segments and thereby manually and or automatically change the firmness value based on user or system feedback. In embodiments not shown both the inner padding and outer padding system can rotate independently. Further, in embodiments, the rotation of the inner and outer padding system can rotate and can be controlled by a click in place rotating knob designed to rotate the inner and outer padding system independently.

Figure 5:
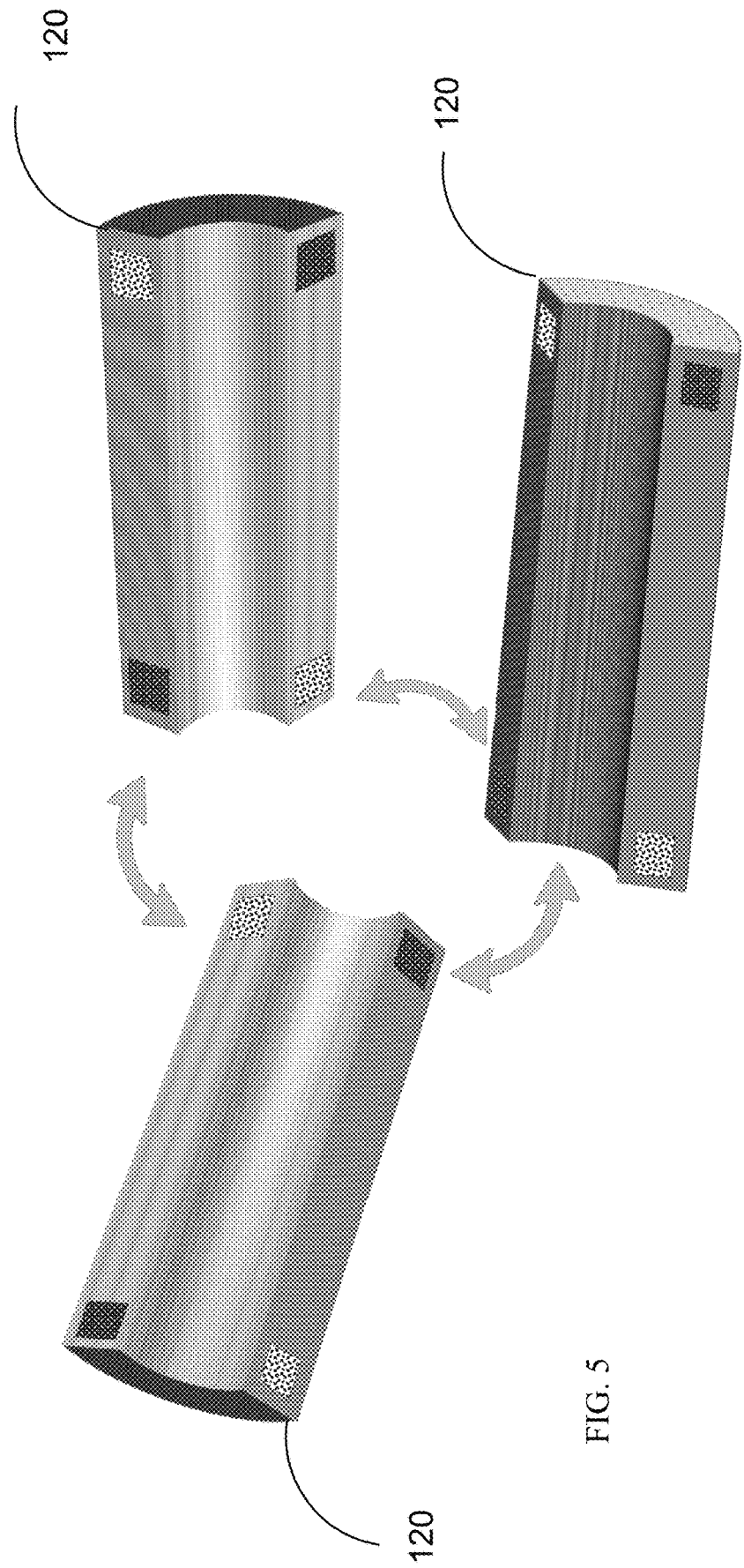
FIG. 5 is a perspective exploded view showing segments of a padding system of an embodiment of the present invention.

As best seen in FIG. 5, the padding segments can include three segments 120 each configured to mate with other segments 120 in order to form a cylindrical shape. The system can include other shapes designed to address muscular and skeletal relief for a user. Such shapes can be contoured and/or shaped to a specific user and/or to address a specific back problem and/or a specific working position that a user may find themselves, such as but not limited to commercial aircraft pilots, military jet fighter pilots, bus drivers, and assembly line workers who either may remain seated or standing for a majority of their time on station. The segments 120 can be mated with one another and can utilize padding segment attachment devices 114 in order to attach the segments to each other.

Figure 6:
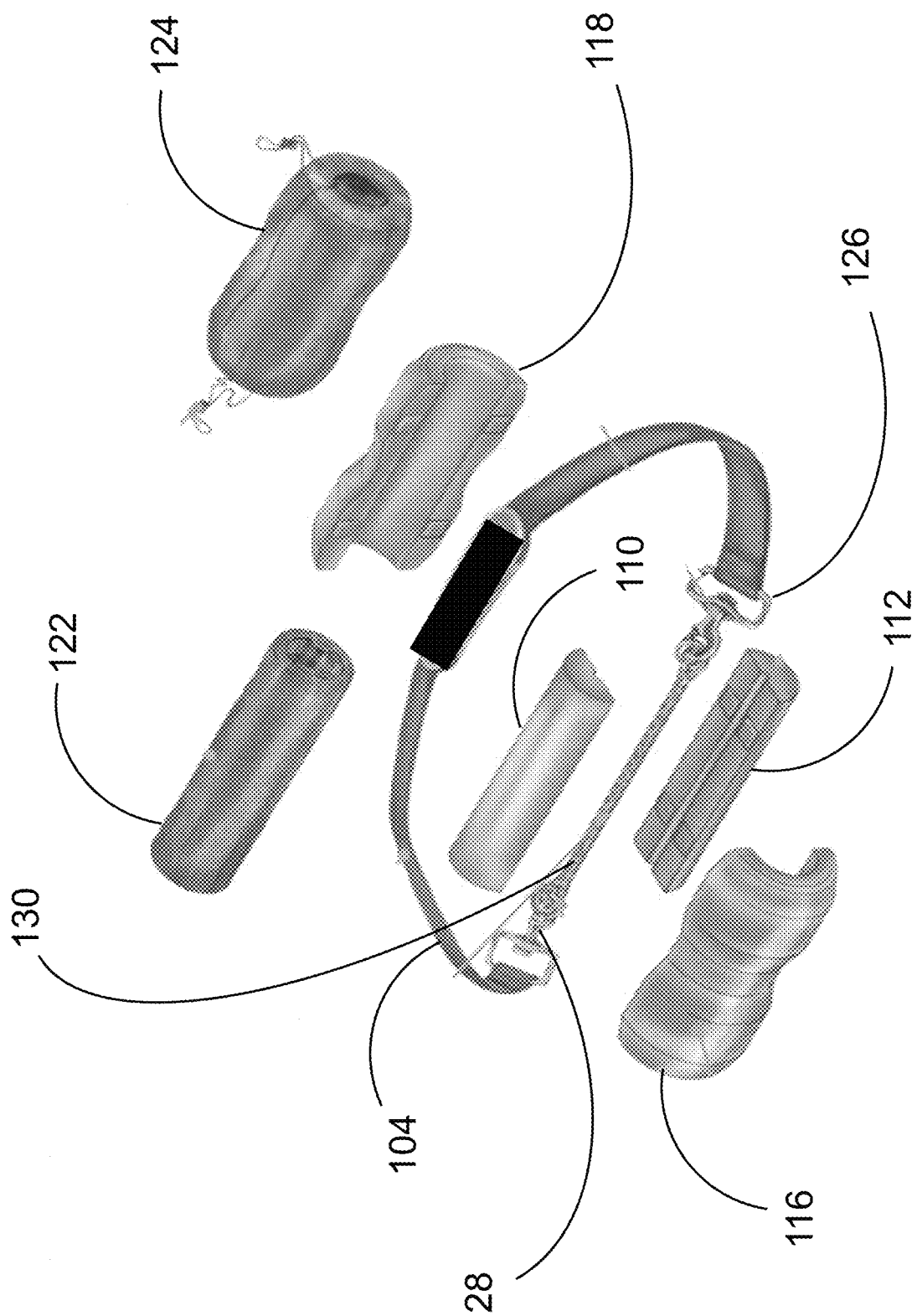
FIG. 6 shows an exploded view of components of an integrated lower back treatment system in an embodiment of the present invention.

FIG. 6 shows an exploded view of an integrated lower back treatment system 100. The system 100 can include an integral unitary inner padding system 122 and it can include an inner padding system with an upper inner padding segment 110 and a lower inner padding segment. The segments mate with one another along the axis of system core 130. The system core 130 can be solid, flexible of a braided cord core, or any other longitudinal component which can be configured to allow inner padding segments and outer padding segments to rotate along the longitudinal axis. The system can include a strap 104. The strap attaches to the core 130 with a combination of swivel eye bolt snap hooks 128 and core fastener D ring 126. The system 100 can also include an outer padding system which can include a right-hand side padding segment 118 and a left-hand side outer padding segment which mate with each other and are configured to encompass the inner segments and are further designed to rotate about the longitudinal axis. Additionally, the rotation of the inner padding segments and outer padding segments occur independently of each other. The system 100 can also include an outer cover 124.

Figure 7:
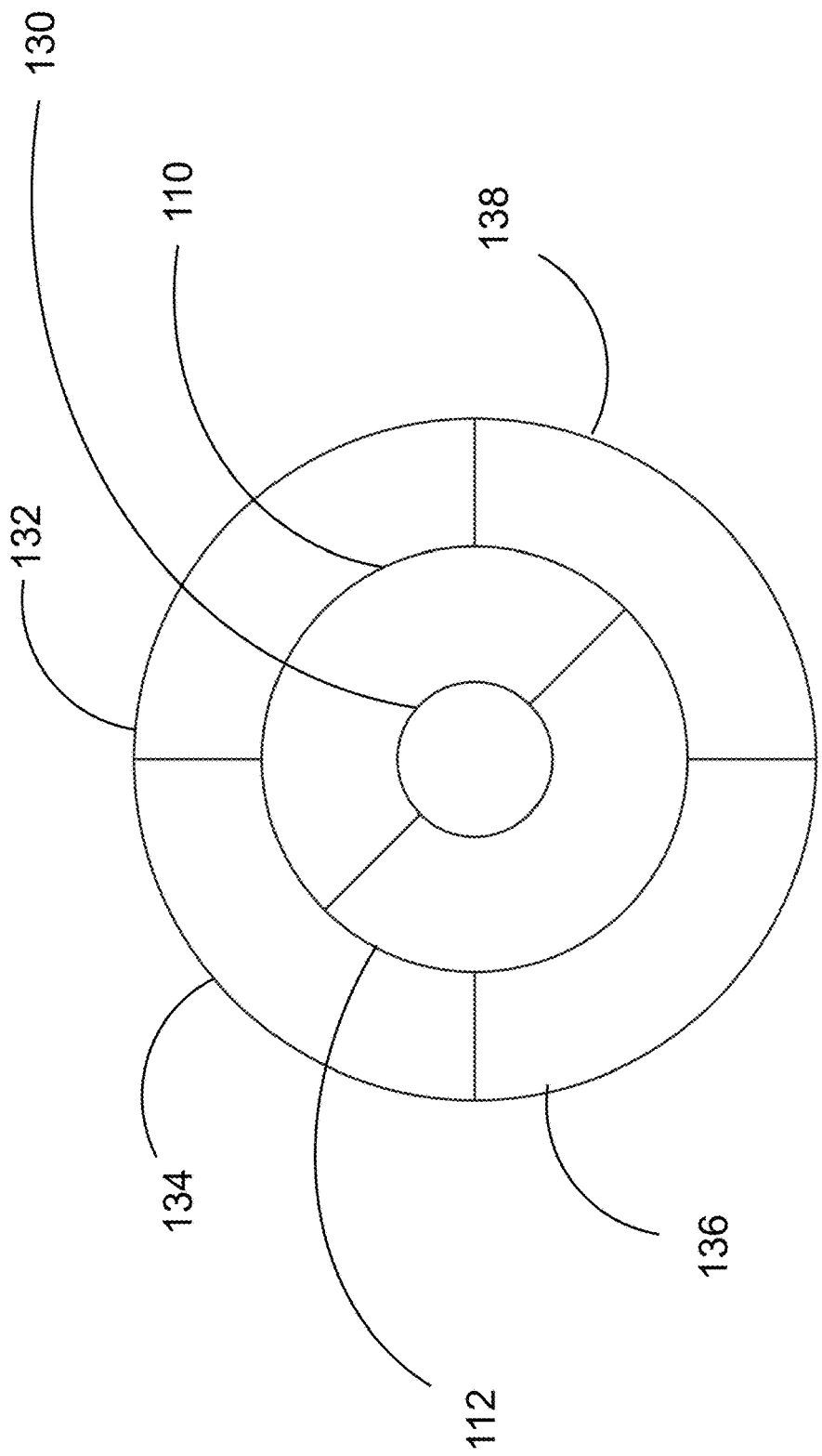
FIG. 7 shows an end view of an assembled integrated lower back treatment system in an embodiment of the present invention.

FIG. 7 shows inner padding segments 110 and 112 circumferentially encompassing the system core 130. Further the outer padding segments 132, 134, 136, and 138 circumferentially encompassing both the system core 130 as well as the inner padding segments 110 and 112. Additionally, each distinct and discrete inner and outer padding segments can include different characteristics such as foam memory, firmness, material composition, organic, non-organic material, such that the composite structure of the assembled padding segments allows a user to rotate the padding segments such that different combinations of aligned padding segments provide a different firmness setting for a user.

Figure 8:
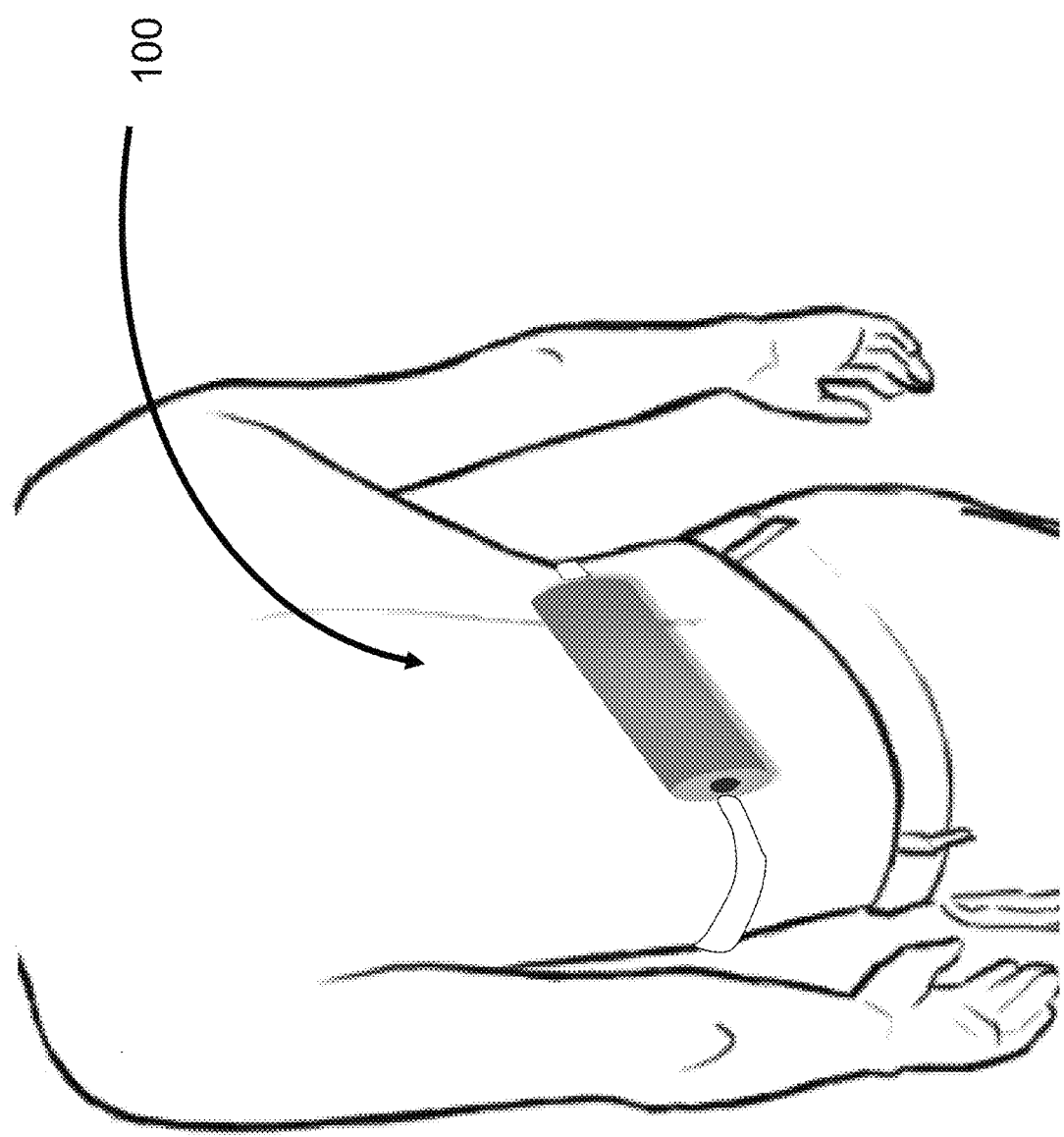
FIG. 8 shows a deployed integrated lower back treatment system on a back of a user.

And as best seen in FIG. 8, an embodiment of an integrated lower back treatment system can be deployed directly on the back of a user to provide lower back treatment. In embodiments, the system 100 can include configurable free-form solid dispersed media. Further, the system 100 can include panelized components with semi-annular, elliptical, or less than circular, 3-dimensional bodies which can include developable strips.

Figure 9:
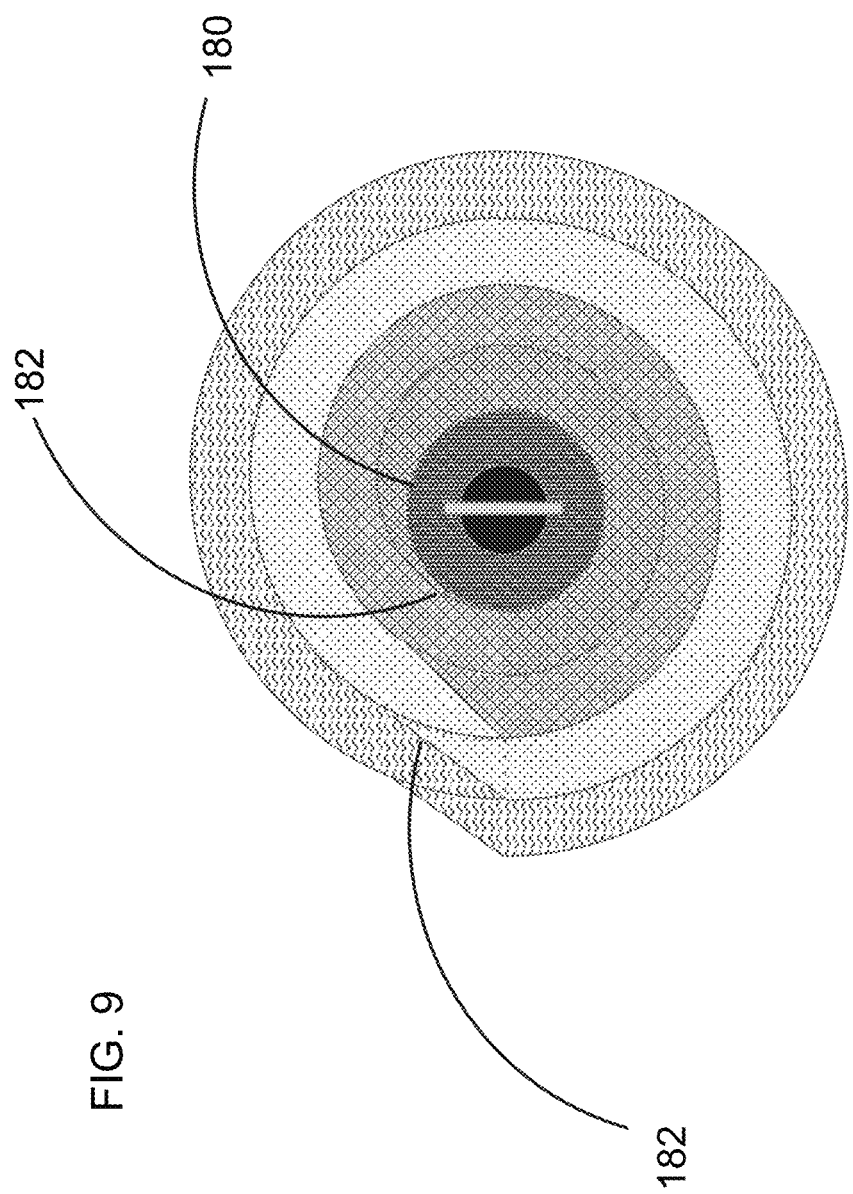
FIG. 9 shows a cross sectional view of an aspect of the integrated lower back treatment system in an embodiment of the present invention.

FIG. 9 displays foam pad layers with leading tapered edges 182 wherein the foam pad layers are configurable with variable densities rolled onto an annular cylinder 180.

In an exemplary embodiment, as described in the following, the system can include devices containing a Strap Assembly made of a Core and a Strap, a first Padding portion, a second Padding portion, a third Padding portion, a fourth Padding portion, an Inner Container, and an Outer Container.

The Core can be an innermost portion of a lumbar device. The Core can have the purpose of resisting tension forces when the user is securing the device to an external seat or a human body. The Core can be a synthetic braided cord where the shape can be longer than it is wide and sufficiently long enough to traverse the length of the assembled device. Both ends of the cord employ a 'D' ring carabiner can be coupled with a Strap. The cord can be centrally attached between with at least 2 straps.

The Strap can be made up of cotton/polyester fabric. The Strap can be made of two independent pieces. One end of each strap has a 'D' ring for coupling with the 'D' ring carabiner on one end of the Core. One Strap can be attached to the Core using said 'D' ring coupling. A second Strap can be similarly be attached using a 'D' ring coupling to the 'D' ring carabiner on the opposite end of the Core. The free end of each Strap, not coupled to the Core, has a snap hook buckle used to fasten to each other. The Strap has a length suitable enough to wrap around a human body and be secured using said snap hook buckle. Further, the Strap has a length sufficient to wrap around a seat and be secured using said snap hook buckle.

The Core together with the attached 2 Straps constitute a Strap Assembly. The Padding has the purpose of providing comfort to the user. The innermost padding layer can be a Core surrounded by the first Padding portion and the second Padding portion. The innermost padding layer can be configured to allow the Core to fit snugly inside diameter of a void defined by the fitting of two opposing channels as described hereinafter.

The first Padding portion and the second Padding portion are complimentary to each other. The first Padding portion and the second Padding portion can be identically shaped. The first Padding portion and the second Padding portion can be identically sized. The first Padding portion length and the second Padding portion length can be shorter than the Core with a distance sufficient to allow user access to the fastening mechanisms that couple the Strap to the Core simultaneously on opposing ends. The first Padding portion and the second Padding portion can each be a semi-annular 3-dimensional shape similar to a 3-dimensional half shaped circle body. The first Padding portion and the second Padding portion can each have differing firmness characteristics. The first Padding portion can have a foam density of very firm. The second Padding portion can have a foam density of firm.

The first Padding portion can have a central channel that traverses the entire length of the Pad. The first Padding portion channel can be shaped as a half cylinder with a radius equal to the outer radius of the Core. As hereinabove noted, the Core fits snugly inside the diameter of the first Padding channel or fits snugly inside the diameter of the second Padding channel.

The second Padding portion can have a central channel that traverses the entire Pad in size and shape identical to the channel on the first Padding portion. Complimentary opposing hook and loop fasteners can be attached to the non-curved faces of the first Padding portion and the second Padding portion so that they are an equal distance from the edges of each respective padding.

The hook and complimentary loop fasteners can be identical in dimensions. The hook and loop are sized to permit the first Padding portion to be secured to the second Padding portion with the Core in place so that the Core cannot slide freely from the said void as formed by the channel of the first Padding portion and the second Padding portion. The void formed from the first Padding portion being secured against the second Padding portion are hereinafter be referred to as Inner Hollow. Further, said hook and loop fasteners are sized to permit the average adult human to separate the first Padding portion from the second Padding portion without undue difficulty.

The first Padding portion has 2 hook fasteners affixed transversely on the flat face and 2 loop fasteners affixed on the opposite face transversely.

The complimentary second Padding portion has 2 hook fasteners affixed transversely on the flat face and 2 loop fasteners affixed on the opposite face transversely. The hook and loop fasteners are positioned in a manner that allow the hook of the first Padding portion to fasten to the opposing loop on the second Padding portion.

During assembly, either the first Padding portion or the second Padding portion are selected. The Core can be laid inside the channel of the selected padding portion. The complimentary padding portion can be attached via hook and loop to form a complete padded layer. It is not a requirement the Strap be affixed during the assembly of the Core and innermost Padding layer. It can be noted that given the pliant nature of the Padding and the Core materials, there can be some minor flexibility in absolute dimensions so long as these differences do not result in a loose fit wherein the Core can slide freely through the Inner Hollow. Further, deviation in the dimensions of the Core and the first Padding portion and the second Padding portion and respective channels must allow the first Padding and second Padding to be securely attached by hook and loop when the Core has been placed centrally within the Inner Hollow.

It can be noted that the assembled Core and inner Padding layer are hereinafter be referred to as the Inner Padding Assembly.

The Inner Container can be a flexible membrane structure which has the purpose of maintaining the configuration of the Inner Padding Assembly. The Inner Container can be made of a synthetic polyester/spandex blend in a ventilated mesh configuration. When not in use, the Inner Container has an amorphous shape. When in use, the Inner Container has a cylindrical shape. The length of the container can be long enough to permit encapsulation of the Inner Padding Assembly when in a slightly stretched (stressed) state. The Inner Container diameter can be similar to the outer diameter of the Inner Padding Assembly with enough diameter to permit encapsulation of the Inner Padding Assembly when in a slightly stretched (stressed) state.

The top and the bottom (base) of the Inner Container are circular. The top and said base each have identical diameter holes that are smaller than the total diameter of the cylinder and large enough to permit the passage of the Inner Padding Assembly when stretched. Each open-ended hole has an elastic woven into the outer edge of the hole to partially close access to the Inner Padding Assembly.

It can be noted that each elasticized hole closure must not frustrate the accessibility of either or both of the 'D' ring carabiners on the Core. It can be further noted that: The user has the option to use the Inner Padding Assembly due to diameter considerations for comfort and pain relief. The user can use the device by enclosing said Inner Padding Assembly using the Inner Container as described hereinbefore and attaching said Straps on both ends of said Core.

It can be noted that the outer Padding layer can be made of the Inner Padding Assembly surrounded by the third Padding portion and the fourth Padding portion. It can be further noted that the outermost Padding layer can be configured to allow the Inner Padding Assembly to fit snugly inside diameter of a void defined by the fitting of two opposing channels as described hereinafter. The third Padding portion and the fourth Padding portion are complimentary to each other. The third Padding portion and the fourth Padding portion can be identically shaped. The third Padding portion and the fourth Padding portion can be identically sized. The third Padding portion length and the fourth Padding portion length can be equal to the length of the first Padding portion.

The third Padding portion and the fourth Padding portion are each a semi-annular 3-dimensional shape similar to a 3-dimensional half shaped circle body. The third Padding portion and the fourth Padding portion can each have differing firmness characteristics. The third Padding portion can have a foam density of medium. The fourth Padding portion can have a foam density of soft.

The third Padding portion can have a central channel that traverses the entire length of the Pad. The third Padding portion channel can be shaped as a half cylinder with a radius equal to the outer radius of the innermost Padding layer. As hereinabove noted, the innermost Padding layer fits snugly inside the diameter of the third Padding channel or fits snugly inside the diameter of the fourth Padding channel.

The fourth Padding portion can have a central channel that traverses the entire Pad in size and shape identical to the channel on the third Padding portion. Complimentary opposing hook and loop fasteners are attached to the non-curved faces of the third Padding portion and the fourth Padding portions so that they are an equal distance from the edges of each respective padding.

The hook and complimentary loop fasteners are identical in dimensions. The hook and loop are sized to permit the third Padding portion to be secured to the fourth Padding portion with the Inner Padding Assembly in place so that the Inner Padding Assembly cannot slide freely from the said void as formed by the channel of the first Padding portion and the second Padding portion. The void formed from the third Padding portion being secured against the second Padding portion can be hereinafter be referred to as Outer Hollow.

Further, said hook and loop fasteners are sized to permit the average adult human to separate the third Padding portion from the fourth Padding portion without undue difficulty. The third Padding portion has 2 hook fasteners affixed transversely on the flat face and 2 loop fasteners affixed on the opposite face transversely. The complimentary fourth Padding portion has 2 hook fasteners affixed transversely on the flat face and 2 loop fasteners affixed on the opposite face transversely. The hook and loop fasteners are positioned in a manner that allow the hook of the third Padding portion to fasten to the opposing loop on the fourth Padding portion. The hook and loop fasteners are positioned in a manner that allow the hook of the third Padding portion to fasten to the opposing loop on the fourth Padding portion. During assembly, either the third or fourth Padding portion are selected. The Innermost Padding layer can be laid inside the channel of selected Padding portion.

The complimentary Padding portion can be attached via hook and loop to form a complete the outer Padded layer. It is not a requirement the Strap be affixed during the assembly of the Innermost Padding layer and outermost Padding layer. It can be noted that given the pliant nature of the outermost Padding and the innermost Padding layer materials, there can be some minor flexibility in absolute dimensions so long as these differences do not result in a loose fit wherein the innermost Padding layer can slide freely through the channel. Further, deviation in the dimensions of the innermost Padding layer and the third Padding portion and the fourth Padding portion and respective channels must allow the third Padding and fourth Padding to be securely attached by hook and loop when the innermost Padding layer has been placed centrally within the channel.

The assembled Inner Padding Assembly and outer Padding layer are hereinafter referred to as Padding Assembly. The Outer Container can be a flexible membrane structure which has the purpose of maintaining the configuration of the Padding Assembly. The Outer Container can be made of a synthetic polyester/spandex blend in a ventilated mesh configuration. When not in use, the Outer Container has an amorphous shape.

When in use, the Outer Container has a cylindrical shape. The length of the Outer Container can be long enough to permit encapsulation of the Padding Assembly when in a slightly stretched (stressed) state. The Outer Container diameter can be similar to the outer diameter of the Padding Assembly with enough to permit encapsulation of the Inner Padding Assembly when in a slightly stretched (stressed) state.

The top and the bottom (base) of the Outer Container are circular. The top and said base each have identically diameter holes that are smaller than the total diameter of the cylinder and large enough to permit the passage of the Padding Assembly when stretched. Each open-ended hole has a drawstring woven into the outer edge of the hole for drawing in the top or the base of the package to selectively close access. It can be noted that the drawstring closure must not frustrate the accessibility of either or both of the 'D' ring carabiners on the Core.

It can be noted that the Inner Container and the Outer Container are used to maintain the user defined configuration as described hereinabove. It can be further noted that a user may elect to use Inner Padding Assembly only with the Inner Container as described hereinafter. It can be still further noted that Inner Container and the Outer Container are similar in construction and appearance with the main difference being dimensions. It can be still further noted that the Inner Container need not be assembled (used) when the Padding Assembly is built.

Said Straps are coupled to the Padding Assembly using said 'D' rings and 'D' ring carabiners. The Straps are configured to secure the Padding Assembly to the user's back such that the outer Padding layer can be disposed adjacent the back of the user's neck and transverses the lumbar spine region such that the first direction of expansion can be toward and substantially normal to the spine effecting relief.

It can be noted as configured, the device yields 8 comfort settings: 2 diameter sizes (1 each for Inner Padding Assembly and Padded Assembly) and 6 padding firmness options Firm, Very Firm, Firm+Medium, Very Firm+Soft, Very Firm+Medium, Firm+Soft) It can be further noted that the number of firmness and diameter settings are governed by the sum of Padding and Diameter options. The Padding can be any shape that makes best use of effecting pain relief by increasing the user selected options. For example, there may be 5 Padding layers (2 Inner Layers and 3 Outer Padding Layers) which would increase the Padding Firmness options by 2 from aforementioned 6 to 8 for a total of 10 comfort settings.

In an embodiment of the invention, the system is configured to customize treatment protocols for individuals. The customization can occur on computing devices such as laptops and mobile devices. Also, the system can include mobile applications. The mobile applications configured to customize treatment programs with data in accordance with algorithms derived from interaction with the individual. The mobile applications can be structured to allow system interface amongst all users of the system.

In some embodiments, the systems and/or methods described above may be executed or carried out by a computing system including a tangible computer-readable storage medium, also described herein as a storage machine, that holds machine-readable instructions executable by a logic machine (i.e. a processor or programmable control device) to provide, implement, perform, and/or enact the above described methods, processes and/or tasks. When such methods and processes are implemented, the state of the storage machine may be changed to hold different data. For example, the storage machine may include memory devices such as various hard disk drives, CD, flash drives, cloud storage, or DVD devices. The logic machine may execute machine-readable instructions via one or more physical information and/or logic processing devices. For example, the logic machine may be configured to execute instructions to perform tasks for a computer program. The logic machine may include one or more processors to execute the machine-readable instructions. The computing system may include a display subsystem to display a graphical user interface (GUI) or any visual element of the methods or processes described above. For example, the display subsystem, storage machine, and logic machine may be integrated such that the above method may be executed while visual elements of the disclosed system and/or method are displayed on a display screen for user consumption. The computing system may include an input subsystem that receives user input. The input subsystem may be configured to connect to and receive input from devices such as a mouse, keyboard or gaming controller. For example, a user input may indicate a request that certain task is to be executed by the computing system, such as requesting the computing system to display any of the above described information, or requesting that the user input updates or modifies existing stored information for processing. A communication subsystem may allow the methods described above to be executed or provided over a computer network. For example, the communication subsystem may be configured to enable the computing system to communicate with a plurality of personal computing devices. The communication subsystem may include wired and/or wireless communication devices to facilitate networked communication. The described methods or processes may be executed, provided, or implemented for a user or one or more computing devices via a computer-program product such as via an application programming interface (API).

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

The present invention has been described with reference to the preferred embodiments, it should be noted and understood that various modifications and variations can be crafted by those skilled in the art without departing from the scope and spirit of the invention. Accordingly, the foregoing disclosure should be interpreted as illustrative only and is not to be interpreted in a limiting sense. Further it is intended that any other embodiments of the present invention that result from any changes in application or method of use or operation, method of implementation which are not specified within the detailed written description or illustrations contained herein are considered within the scope of the present invention.

Insofar as the description above and the accompanying drawings disclose any additional subject matter that is not within the scope of the claims below, the inventions are not dedicated to the public and the right to file one or more applications to claim such additional inventions is reserved.

What is claimed:

1. An integrated lower back treatment system comprising:
   a central core;
   attachment devices positionable on longitudinal ends of the central core;
   a strap, wherein an end of the strap connects with a first longitudinal end of the central core with a first attachment device of the attachment devices and an opposite second end of the strap connects to an opposite second longitudinal end of the central core with a second attachment device of the attachment devices;
   a padding assembly, wherein the padding assembly includes an inner padding system and an outer padding system, wherein each of the inner padding system and outer padding system comprises a plurality of padding segments arranged to allow the plurality of padding segments to mate with each other forming a ring shape surrounding the central core and wherein the padding segments are annular segment panels structured with differing firmness characteristics such that when the plurality of padding segments are rotated about a longitudinal axis of the central core, a user of the integrated lower back treatment system will experience different firmness values dependent upon a position of the rotated padding segments on a lower back of the user.

2. The integrated lower back treatment system of claim 1 wherein the inner padding system is rotatable about the longitudinal axis of the core and wherein the outer padding system is rotatable about the longitudinal axis of the core and wherein rotation of the inner padding system is independent of rotation of the outer padding system.

3. The integrated lower back treatment system of claim 2 wherein the rotation of the inner padding system and the rotation of the outer padding system is accomplished with a click to turn device.

4. The integrated lower back treatment system of claim 1 further comprising a vibration device configured to interact with the integrated lower back treatment system to provide vibration movements to a lower back of a user designed to stimulate nerves, relieve muscular tension, decrease stress, and improve circulation.

5. The integrated lower back treatment system of claim 1 further comprising a cooling device and/or a heating device configured to interact with the integrated lower back treatment system to provide temperature changes to a lower back of a user designed to stimulate nerves, relieve muscular tension, decrease stress, and improve circulation.

6. The integrated lower back treatment system of claim 1 wherein the inner padding system and the outer padding system define layers.

7. The integrated lower back treatment system of claim 6 wherein the layers include contiguous padding.

8. The integrated lower back system of claim 1 wherein the system is controlled remotely with a mobile application.

9. The integrated lower back system of claim 1 wherein the central core includes cylindrical, oval, triangle, rectangular, or star shapes.

10. The integrated lower back system of claim 1 wherein the longitudinal axis of the central core is curved.

11. The integrated lower back system of claim 1 wherein the padding assembly includes contoured outer surfaces and circular, oval, triangle, rectangular, or star shapes.

12. The integrated lower back system of claim 1 wherein the inner padding system and/or the outer padding system define cylndrical shapes.

13. The integrated lower back system of claim 1 wherein the inner padding system and/or the outer padding system comprise curved shapes.

\* \* \* \* \*